United States Patent [19]
Chien et al.

[11] Patent Number: 5,089,099
[45] Date of Patent: Feb. 18, 1992

[54] FIELD AMPLIFIED POLARITY SWITCHING SAMPLE INJECTION IN CAPILLARY ZONE ELECTROPHORESIS

[75] Inventors: Ring-Ling Chien, San Jose; Dean S. Burgi, Palo Alto, both of Calif.

[73] Assignee: Varian Associates, Inc., Palo Alto, Calif.

[21] Appl. No.: 621,169

[22] Filed: Nov. 30, 1990

[51] Int. Cl.⁵ .............................................. B01D 57/02
[52] U.S. Cl. ............................... 204/180.1; 204/299 R
[58] Field of Search ............. 204/299 R, 182.1, 182.8

[56] References Cited

U.S. PATENT DOCUMENTS

| | | | |
|---|---|---|---|
| 4,675,300 | 6/1987 | Zare et al. | 436/172 |
| 4,909,919 | 3/1990 | Morris et al. | 204/299 |

FOREIGN PATENT DOCUMENTS

| | | |
|---|---|---|
| 0329341 | 8/1989 | European Pat. Off. |
| 0329341A2 | 8/1989 | European Pat. Off. |
| 0361750A2 | 4/1990 | European Pat. Off. |

OTHER PUBLICATIONS

Gordon, et al, "Capillary Electrophoresis," Science, 242 (1988) 224-228.

Hjerten et al. "Some Aspects of the Use of 'Continuous' and 'Discontinuous' Buffer Systems in Polyacrylamide Gel Electrophoresis," Analytical Biochemistry, 11(1965) 219-223.

Hjerten, Stellan, "High Performance Electrophoresis: the Electrophoretic Counterpart of High-Performance Liquid Chromatography," Journal of Chromatography, 270 (1983) 1-6.

Huang et al., "Bias in Quantitative Capillary Zone Electrophoresis Caused by Electrokinetic Sample Injection," Anal. Chem., 60(1988) 375-377.

Gross et al., "Indirect Fluorimetric Detection and Quantification in Capillary Zone Electrophoresis of Inorganic Anions and Nucleotides," Journal of Chromatography, 480 (1989) 169-178.

Morning et al., "Analytical Aspects of an Automated Capillary Electrophoresis System," IC-GC, vol. 8, No. 1 (1989) 34-46.

Jorgenson et al., "Capillary Zone Electrophoresis," Science, 222 (1983) 266-272.

Jorgenson et al., "Zone Electrophoresis in Open-Tubular Glass Capillaries," Analytical Chemistry, vol. 53, No. 8 (1981) 1298-1302.

Huang et al., "Analysis of Factors Causing Peak Broadening in Capillary Zone Electrophoresis," Journal of Chromatography, 480 (1989) 95-110.

Rose et al., "Characterization and Automation of Sample Introduction Methods for Capillary Zone Electrophoresis," Anal. Chem., 60 (1988) 642-648.

Mikkers et al., "Concentration Distributions in Free Zone Electrophoresis," Journal of Chromatography, 169 (1979) 1-10.

Huang et al., "Effect of Electrolyte and Sample Concentration on the Relationship Between Sensitivity and Resolution in Capillary Zone Electrophoresis Using Conductivity Detection," Journal of Chromatography, 480 (1989) 285-288.

Primary Examiner—John Niebling
Assistant Examiner—Caroline Koestner
Attorney, Agent, or Firm—Peter J. Sgarbossa; Sheri M. Novack

[57] ABSTRACT

An improved electroinjection method of introducing a sample having positive and negative ions into a capillary column for CE or CZE process by introducing a short plug of a low concentration buffer before introducing the sample into the column which results in increasing amount of charged ions of the sample introduced in the capillary column due to increasing the electric field at the injection point. A method for efficiently introducing both positive and negative ions is also shown.

43 Claims, 4 Drawing Sheets

FIELD AMPLIFIED POLARITY SWITCHING SAMPLE INJECTION IN CAPILLARY ZONE ELECTROPHORESIS

FIELD OF THE INVENTION

The invention relates to methods for electric separation and detection of sample components by differential electrokinetic migration in a narrow capillary tube, and more particularly to methods for introducing sample into the capillary.

BACKGROUND OF THE INVENTION

Capillary electrophoresis (CE) or specifically capillary zone electrophoresis (CZE) is a known efficient separation technique useful for fast, high resolution and efficient separation of charged species in solutions. High resolution in CZE technique requires the introduction of a small volume sample, i.e., in the range of 5 to 50 nl.

There are a number of methods for injecting such volume of sample into the capillary column. The two principal sample injection techniques are electrokinetic and hydrostatic injection as described in the following articles: Jorgenson, J. W. and Lukacs, K. D., *Science*, 1983, v. 222, p. 266–272, Wallingford R. A., and Ewing A. G. *Anal. Chem.*, 1987, v 59, p. 678–681.

Electrokinetic injection is performed through the pumping activity of electroosmosis and electrophoresis. Samples are introduced at one end of a buffer filled capillary and, stimulated by an applied high-voltage electric field, move towards the other end of the capillary tube. Samples are usually injected at the positive high-voltage end due to electroosmotic flow that carries solutes, regardless of charge, toward the negative electrode. This injection technique, while simple and easily controlled, can affect the introduced quantities of different sample components since some sample species will have higher electrokinetic mobilities than other species, (see Huang, X., et al., *Anal. Chem.*, 1988, v. 60, p. 375–377).

Hydrostatic injection is characterized by physically introducing samples in the capillary and might be referred to as suction, pressure, or gravity injection. In this method one end of the buffer filled capillary tube is removed from the buffer reservoir and introduced into a sample solution which is raised vertically above the capillary outlet. This height difference between the level of the sample solution and the buffer reservoir yields a hydrostatic pressure which siphons sample into the capillary. Alternatively, for automatically introducing a sample into the capillary, a vacuum can be applied to the end of the capillary tube. However, hydrostatic injection increases the zone broadening effect due to laminar flows generated during the injection, and influences the separation efficiency in zone electrophoresis. Comparison of electrokinetic and hydrostatic injection techniques indicate that electrokinetic introduction is preferably because it is simpler and produces less zone broadening.

DISADVANTAGE OF THE PRIOR ART

In conventional electro-injection in CZE, the buffer solution that is used for sample preparation and the buffer solution inside the capillary column have the same concentrations. The number of ions injected into the column under this condition is rather limited, especially due to the fact that negative ions can not move against the electric fields, assuming the column wall is negatively charged. Preparing samples in a low conductivity solution, e.g., $H_2O$, and injecting the sample solution electrokinetically into the column, one achieves a field enhancement at the injection point. The injected amount of positive ions will be proportional to this enhancement factor. However, if the injection is accomplished by changing the capillary column input directly from the high conductivity buffer to the low conductivity sample solution, the buffer boundary at the input end of the capillary column is disturbed and the electric field at the injection point might not get amplified properly. In addition, the negative ions, not only will not be enhanced, but will be repelled from the column by this high electric field.

SUMMARY OF THE INVENTION

The foregoing disadvantage of the prior art sample introduction methods for capillary zone electrophoresis are overcome by the present invention. According to the invention, an improved electrokinetic injection technique is used for introducing a sample electrically into the capillary column by injecting a short plug of low conductivity buffer before sample introduction, for a short period of time which is relatively short in comparison to analysis time. The analysis time is a time interval between the sample introduction into the capillary columns and complete detection of its components. The short plug of the low conductivity buffer is introduced into the capillary column by hydrostatic or electroinjection.

In addition, since the electroosmotic velocity of the bulk solution is much slower than the electrophoretic velocity of sample ions under the enhanced field, one can inject and concentrate both positive and negative ions into the column by switching the polarity of the electrodes at the proper time. For example, one can first inject positive ions for a time period of $t_1$, then switch the polarity to inject negative ions for time period $t_2$. When $t_2 = t_1/2$ the number of positive and negative ions injected will be roughly equal for the reasons described below. Furthermore, one can also achieve selected charge discrimination by injecting either positive or negative ions only. We call this Field Amplified Polarity Switching Injection (FAPSI).

Experiment data was obtained with an electrolyte solution containing 100 mM 2-N-(morpholino)ethanesulfonic acid (MES) and histidine (HIS). For field amplified sample injection (FASI), a stock solution contained 2.1 mg PTH-Arginine and 2.0 mg PTH-Histidine in 10 ml of $H_2O$ was made. The sample solution was further diluted down to about $10^{-4}$, $10^{-5}$ or $10^{-6}$ M, respectively, and injected after inserting a small plug of water in the column by application of a voltage of 3 kV in 10 sec. By initial introduction of the short water plug a high electric field intensity is built up at the column inlet from the beginning of the injection. A hundred fold enhancement in the sensitivity was confirmed experimentally at low sample concentration.

For field-amplified polarity-switching injection (FAPSI), a 2.8 mg PTH-Aspartic acid and 3.2 mg PTH-Glutamic acid were added into the previous stock sample solution with PTH-Arginine and PTH-Histidine. A $\pm 5$ kV switchable power supply was used for injection. Several different time programming injection experiments were tried, and the enhancement in the sensitivity for both positive and negative ions was confirmed.

Gravity-assisted injection was also performed using the above materials.

DETAILED DESCRIPTION

Technical Background

Figure 1:
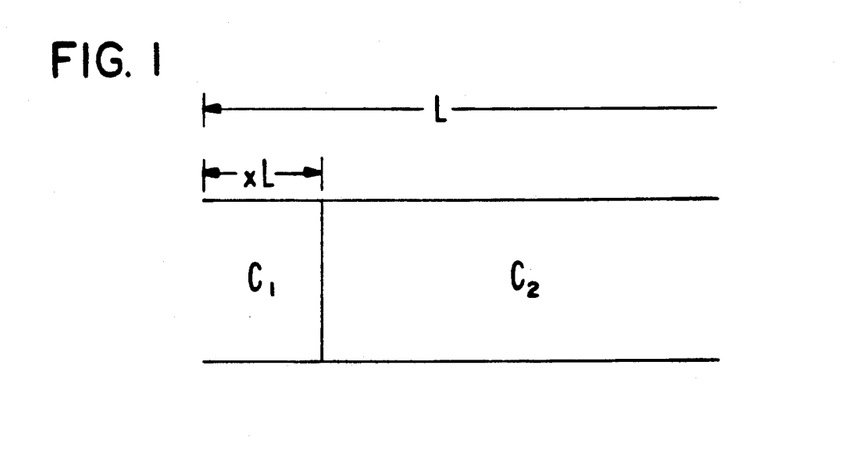
FIG. 1 is a schematic of a capillary column filled with an electrolyte with different concentrations, $C_1$ and $C_2$.

Consider a capillary column with length L filled with buffering medium having different concentration in two or more regions as shown on FIG. 1.

In a useful and substantially accurate model of a capillary system, the total resistance R of the column will be:

$$R = (\rho_1 x + \rho_2(1-x))L/A \quad (1)$$

Where $\rho_1$, $\rho_2$ are the resistivities of buffer with concentration $C_1$ over the length of $xL$, and $C_2$ over the length of $(1-x)L$ respectively, and A is the cross section of the column, x is fraction of the capillary length occupied by the media with concentration $C_1$; i.e., $0 \leq x \leq 1$.

For a column filled with buffering medium of a single concentration in the capillary column, i.e., $x=1$ or $x=0$, we have $R = R_1 = \rho_1 L/A$, or $R = R_2 = \rho_2 L/A$. Substituting the resistivities in Eq (1) with the resistances of the column with straight buffer gives the total resistance of aforementioned system.

$$R = R_1 x + R_2(1-x) \quad (2)$$

If the voltage V is applied across the column, the electric current I will be:

$$I = V/R = V/(R_1 x + R_2(1-x)) \quad (3)$$

Since the electric field E is a product of the current density and resistivity, the local field $E_1$ and $E_2$ in the two regions with different concentrations are $$E_1 = \rho_1 I/A = IR_1/L \quad (4)$$

and $$E_2 = \rho_2 I/A = IR_2/L \quad (5)$$

Substituting into Eq (3), Eq (4) and (5) respectively the expression result in $$E_1 = E_0 R_1/(R_1 x = R_2(1-x)) \quad (6)$$

and $$E_2 = E_0 R_2/(R_1 x + R_2(1-x)) \quad (7)$$

Where $E_0 = V/L$ is the field strength of a uniform system, filled with buffer 1 or buffer 2.

Figure 2:
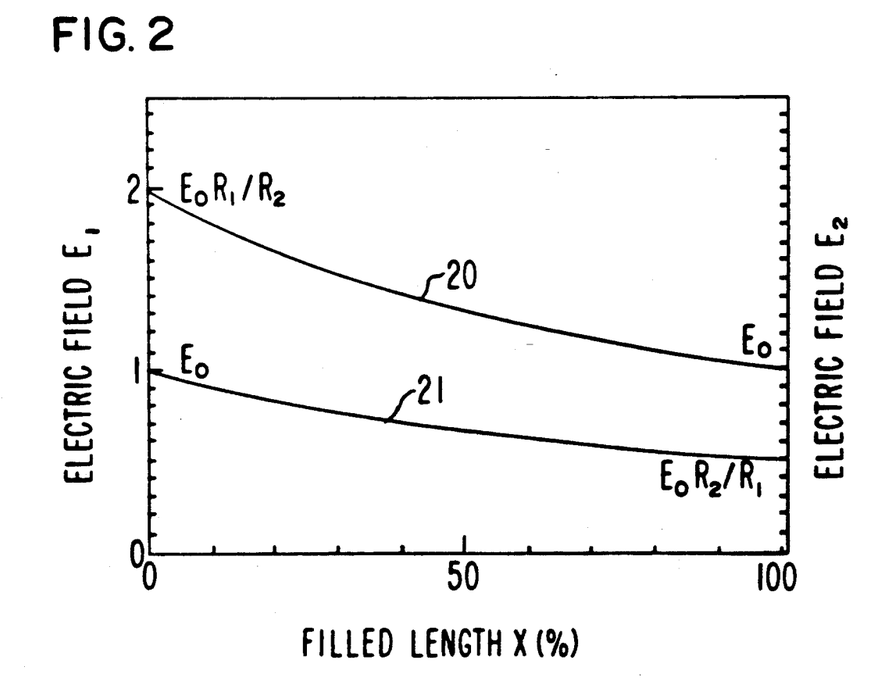
FIG. 2 is a plot of the local electric field as function of filled length.

FIG. 2 element 20 shows a plot of Eq (6) and element 21 shows the plot of Eq (7) for $R_1/R_2 = 2$.

While the absolute value of the electric field in the regions of buffer 1 and 2 will depend on the length of the buffer regions, the ratio between them will remain constant, and only depends on their resistivities, which in general are inverse proportional to the concentrations so $$\frac{E_1}{E_2} = \frac{C_2}{C_1} \quad (8)$$

The Eq (8) indicates that the ions inside the lower concentration region will experience higher electric field and hence will move faster than the ions inside the higher concentration region. Once these faster ions pass the concentration boundary, they will experience lower electric field, slow down, and stack into higher concentration. As a consequence, this concentration boundary is a stationary boundary with respect to the electroosmotic flow.

For analyzing the electroosmotic flow property in a mixed concentration system, a double layer model is used. In this well known model (see Gordon, M. J., et al. *Science*, 1988, v. 242, p. 225), the electroosmotic mobility is proportional to the zeta potential, i.e., the dielectric constant, at the silica/water interface. This zeta potential is proportional to the product of the charge on the interface and the Debye length, a characteristic distance beyond which the electric field of a charged particle is shielded by particles having charges of the opposite sign. Since the Debye length is inversely proportional to the square root of the ionic strength, or the concentration, as the concentration increases, the electroosmotic mobility decreases.

In columns with a single phase buffer, the electric field strength is uniformly distributed along the column. Consequently, the electroosmotic velocity, which is equal to the electroosmotic mobility times the electric field strength, is also a constant.

If concentration is nonuniform, the electric field strength will be nonuniform also according to Eqs. (6) and 7). In addition, the electroosmotic mobility is larger in the lower concentration region, which further enhances the difference in the local electroosmotic velocities between the two regions.

However, the bulk solution has to move with a single averaged velocity. The difference of the local electroosmotic velocities and this bulk velocity will generate a hydrostatic pressure across the local regions.

The high osmotic velocity of the input section is then balanced by the hydrostatic pressure which drives fluid back along the axis of the column, while the fluid in the second section is driven forward along the axis, relative to the lower osmotic flow. The boundary now behaves as a soft wall between the two regions with different concentrations. If the leading buffer has a slower electroosmotic velocity than the bulk velocity, this "soft wall" will be pushed forward by the trailing buffer, if the leading buffer has a faster electroosmotic velocity, it will pull the "soft wall" along.

If the resistance to laminar flow is less than the resistance to osmotic flow, the average velocity $v_b$ is:

$$v_b = x v_{e1} + (1-x) v_{e2} \tag{9}$$

where $v_{e1}$, $v_{e2}$ are the local osmotic velocities in the two concentration regions 1 and 2, respectively. Equation (9) shows that the boundary moves with a weighted average of electroosmotic velocities.

The local electroosmotic velocity is $$v_{ej} = \frac{V_{eoj} \rho_j}{\rho_1 x + \rho_2 (1-x)} \tag{10}$$

where $v_{eoj}$ is the electroosmotic velocity is a column filled with pure buffer j. Substitution of Eq. (10) into Eq. (9), yields:

$$v_b = \frac{v_{eo1} \rho_1 x}{\rho_1 x + \rho_2 (1-x)} + \frac{v_{eo2} \rho_2 (1-x)}{\rho_1 x + \rho_2 (1-x)}$$
$$= v_{eo2} + \frac{\Delta v_{eo} \rho_1 x}{\rho_1 x + \rho_2 (1-x)} \tag{11}$$

where $\Delta v_{eo} = v_{eo1} - v_{eo2}$ is the difference in the osmotic velocities of pure systems. Eq. (1) shows that the average osmotic velocity of the system is not only weighted over the lengths of their components but also weighted over their partial resistances.

If we now dissolve samples in a lower concentration buffer, and inject them electrokinetically into the column, the electric field at the injection point will be much stronger than the electric field in the capillary column. If the injection buffer has the same composition as the capillary column buffer, the electric field ratio is from Eq. (8):

$$\frac{E^{(i)}}{E^{(c)}} = \frac{C_b^{(c)}}{C_b^{(i)}} = r$$

where $E^{(i)}$, $E^{(c)}$ and $C_b^{(i)}$, $C_b^{(c)}$ are the electric fields and buffer concentrations at the injection point and in the column, respectively.

While the electrophoretic velocity for ion species i at the injection point is proportional to the enhanced field, $v_{ep} = \mu_{ep} r E_o$, the average electroosmotic velocity $v_{eo}$ of the bulk solution in a mixed buffer system changes insignificantly, $v_{eo} \approx \mu_{eo} E_o$. For $r >> 1$, the ions are injected into the capillary column faster than the neutral solution.

The total amount of ion species injected into the column is given by $$N_i = \int_0^t A C_i^{(i)} (v_{eo}(t) + v_{ep}(t)) \, dt \tag{12}$$

where A is the cross sectional area of the capillary and t is the injection time. To calculate the total amount of ions injected into the column and the plug length, knowledge of $v_{eo}$, $E^{(i)}$ and $E^{(c)}$ with respect to the injection time t is required. For a short injection time, they could be assumed constant, and Eq. (12) gives $$N_i = C_i^{(i)} A (\mu_{eo} + r \mu_{epi}) E_o t. \tag{13}$$

Since the electrophoretic velocity exceeds the electroosmotic velocity at the injection point, some of the injected ions would pass the boundary and move into the low field region. Inside the capillary column, the injected ions will now be distributed into the two regions with difference concentrations. In the region limited by the electroosmotic flow, ions have the same concentration as in the original sample solution. In the low field region, the ion concentration is enhanced by the same factor r, i.e., $C_i^{(c)} = r C_i^{(i)}$. Equation (13) can be rewritten as $$N_i = C_i^{(i)} A X^{(i)} + C_i^{(c)} A X^{(c)} \tag{14}$$

where $X^{(i)} = \mu_{eo} E_o t$ and $X^{(c)} = \mu_{epi} E_o t$ are the plug lengths of the sample ions in low and high buffer concentration regions, respectively. Eventually, all sample ions will migrate into the high concentration region and stack into narrow bands according to their electrophoretic mobilities.

For the sample injection using pure water, the theoretical enhancement factor might be several hundreds if a 10 mM buffer was used. We have obtained an enhancement factor of about ten when the capillary column was directly switched from the high conductivity buffer reservoir to the low conductivity aqueous sample solution.

The lower field enhancement may be explained by the perturbation of electric field in the region close to the boundary. Injection of short plug of low concentration buffer or water prior the sample introduction maintains high electric field at the injection point and an enhancement of a hundred were obtained experimentally.

Field-amplified sample injection works for positive ions only. The negative ions, will be pushed in the opposite direction by the high electric field. However, since the electroosmotic velocity of the bulk solution is much slower than the electrophoretic velocity of the sample ions under the enhanced field, we have discovered that it is possible to inject and concentrate both positive and negative ions into the columns by switching the polarity of the electrodes at the proper time. We call this technique Field-Amplified Polarity-Switching Injection (FAPSI).

Figure 3A:
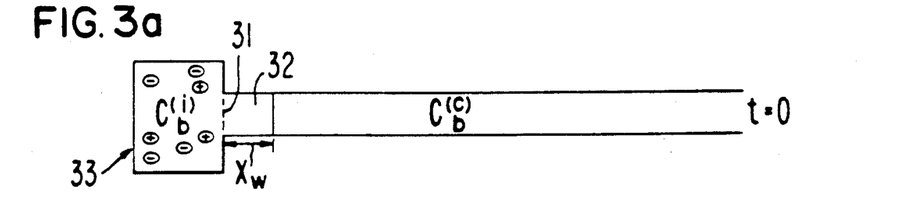
FIGS. 3(a), 3(b), 3(c), and 3(d) are schematic diagrams of the field-amplitude polarity-switching injection in CZE.
Figure 3B:
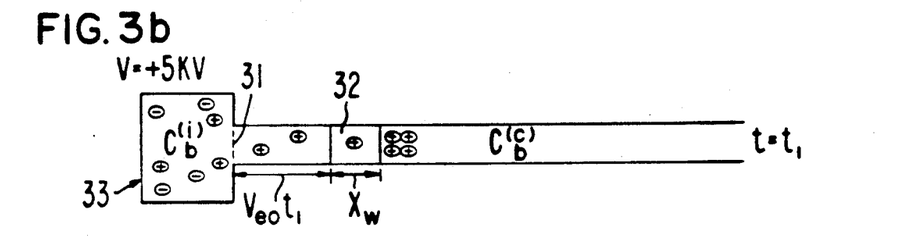

In FAPSI, samples of both positive and negative ions are prepared in the low conductivity buffer. As shown in FIG. 3(b), we can inject a large amount of positive ions under a positive high voltage with respect to the outlet end of the column for a time period $t_1$. To obtain maximum enhancement, we can introduce a short plug of a low conductivity buffer into the column end 31 before sample injection. A short plug, 32, of low conductivity buffer, $x_w$, will be injected electroosmotically into the column and establishes a concentration boundary. Most of the positive ions will stack after the boundary into the high concentration region. The lengths of the low conductivity region, $x_n$, inside the column after $t_1$ are $$x_n = v_{eo} t_1 + x_w \tag{15}$$

Figure 3C:
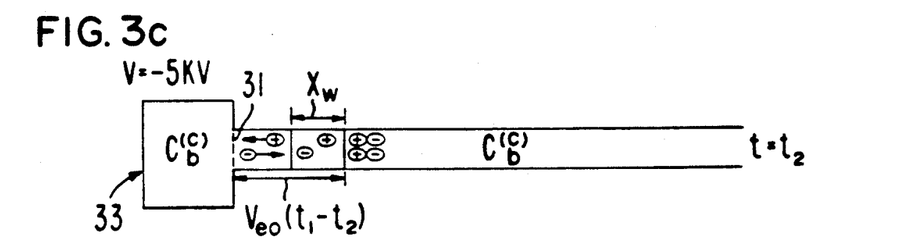

We then switch the voltage to the opposite polarity and cause the electroosmotic flow to migrate in the other direction as shown in FIG. 3(c). Since the electric field at the injection end of the column is high, the negative ions which now have a very high electrophoretic velocity overcome the slow electroosmotic flow and migrate into the column. This reverse polarity voltage can last for $t_2$ such that the positive ions will also remain inside the column.

The plug length of low conductivity region is $$x_n = v_{eo}(t_1 - t_2) + x_n$$

The amount of positive and negative ions injected into the column are $$N^{(+)} = C_i^{(+)} A (v_{eo} + \mu_{ep_i}^{(+)} r E_o)(t_1 - t_2)$$

and $$N^{(-)} = C_i^{(-)} A (\mu_{ep_i}^{(-)} r E_o - v_{eo}) t_2.$$

respectively, where r is the field enhancement factor. For $t_2 = t_1/2$ and $\mu_{ep}^{(-)} \approx \mu_{ep}^{(+)}$, we have $N^{(-)} = N^{(-)}$, if $r \gg 1$.

Figure 3D:
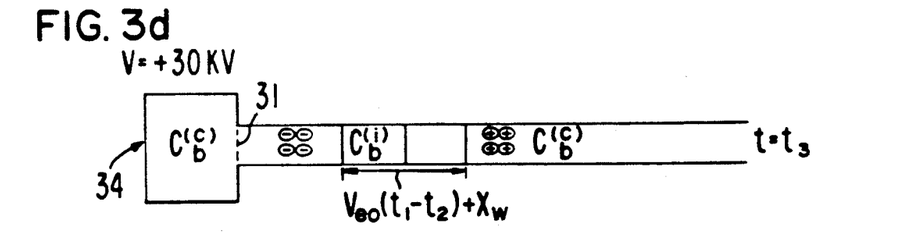

After injection of both positive and negative ions, the inlet end of the capillary column is connected from low conductivity reservoir 33 back to the high conductivity buffer reservoir 34. The polarity of the high voltage is also switched, via switch 35, back to the normal setting connected to the high negative voltage and the normal separation process starts as shown in FIG. 3(d).

PREFERRED EMBODIMENT OF THE INVENTION

Figure 4:
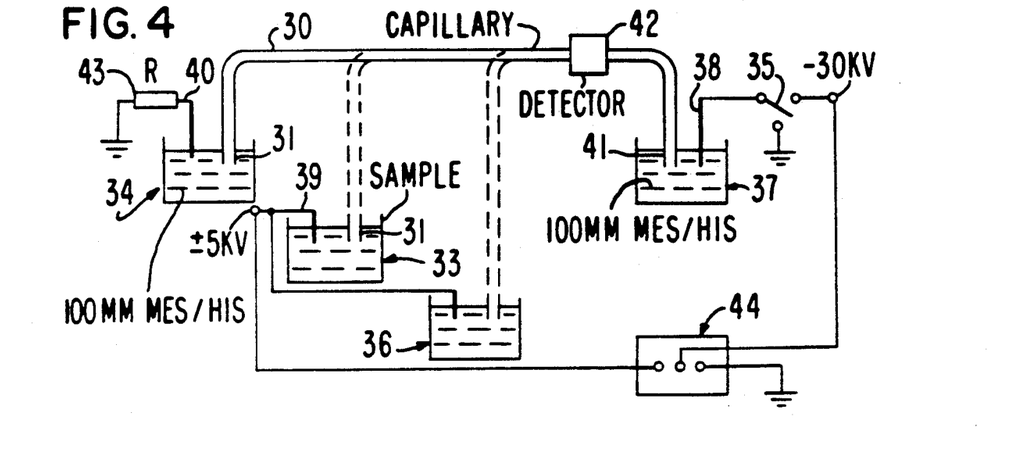
FIG. 4 is a schematic diagram of the CZE system according to the present invention.

A FAPSI method in CZE were performed using a CZE system developed by the inventors. A schematic diagram of the system is shown in FIG. 4. As shown in FIG. 4, apparatus includes a capillary column 30 with inlet end 31 and outlet end 41.

A high concentration electrolyte is supplied to capillary column 30 from a reservoir 34 at the inlet end 31. A reservoir 37 at the outlet end 41 of the capillary column 30 collects the electrolyte of after it has passed through the column. Two more reservoirs may be used for sample introduction. One reservoir 36 is filled with low concentration electrolyte or water. The other reservoir 33 is filled with the sample solution prepared in the low concentration electrolyte or water.

A high voltage is applied between the inlet and the outlet ends of the column, causing the electrolyte to move from one end to the other end. The system is supplied with a power supply 44 providing three high voltages; two for injection, i.e., $\pm 5$ kV dc, the other for separation, i.e., 30 kV dc.

The ground end of the power supply for injection is connected to a wire 38, preferably platinum, in the reservoir at the outlet end of the column. The high voltage end of the injection power supply 44 which can be switched between $\pm 5$ kV, is connected to a wire 39, preferably platinum, in the reservoir filled with low concentration electrolyte 36 or the reservoir 33 filled with the sample solution. This power supply 44 is connected to the system only during sample introduction.

The ground end of the power supply 44 for separation is connected to a wire 40, preferably platinum, in the reservoir filled with high conductivity at the inlet end 31 of the column 30. The high voltage end of the power supply 44, which is set at $-30$ kV, is connected to a platinum wire 38 connected to the reservoir at the outlet end 41 of the column 30 through switch 35.

Electrophoresis may be carried out in any capillary column, as is well known in the art, such as a 75 $\mu$m i.d., 360 $\mu$m o.d., fused-silica capillary column (Polymicro Technologies, Phoenix, Ariz.) of 100 cm length. Any suitable column detector, such as on-column UV high-performance liquid chromatography absorption detector 42 (TASCO, Tokyo, Japan) may be used. The distance from the injection point to detection point is adjustable. For these experiments it was held at 75 cm. Electroinjection was used for introducing a sample into the column.

In addition to the optical signal the electrophoresis current may be monitored by measuring the voltage drop across a resistor 43 in series with the capillary column.

SAMPLE INTRODUCTION PROCEDURES

For introduction of positive ions only the column was filled with 100 mM MES/HIS buffer. The inlet end 31 of the capillary column 30 was transferred from the 100 mM MES/HIS buffer to the buffer reservoir containing H$_2$O. A short plug of H$_2$O was injected into the column 30 by applying $+5$ kV with respect to the outlet end 41 of the column 30 for 30 sec or by gravity injection at 5" high for 10 sec. The positive sample ions were then injected electrically into the column by transferring the inlet end of the column from the H$_2$O reservoir to the fourth reservoir 36 containing the sample dissolved in the water. A potential of $+5$ kV with respect to the outlet end of the column was then applied for 10 sec. causing a small plug of positive ions to electromigrate into the column. The inlet end 31 of column 30 was transferred back to 100 mM MES/HIS buffer and the separation is started with 30 kV applied to that the inlet end 31 is positive with respect to the outlet end 41 of the column 30.

For introduction of negative ions only, the column was filled with 100 mM MES/HIS buffer. The inlet end 31 of the capillary column 30 was transferred from the 100 mM MES/HIS buffer to the buffer reservoir 36 containing H$_2$O. A short plug of H$_2$O was injected into the column 30 by applying $+5$ kV with respect to the outlet end of the column 30 for 30 sec or by gravity injection at 5" for 10 sec. The negative sample ions were injected electrically into the column 30 by transferring the inlet end 31 of the column 30 from the H$_2$O reservoir to the fourth reservoir 33 containing the sample dissolved in the water. A $-5$ kV potential with respect to the outlet end of the column was then applied for 10 sec. causing a small plug of negative ions to electromigrate into the column 30. The inlet end 31 of column 30 was then transferred back to 100 mM MES/HIS buffer, starting the separation with a $+30$ kV applied at the inlet end 31 with respect to the outlet end 41 of the column 30.

For injecting both positive and negative ions the column was filled with 100 mM MES/HIS buffer. The inlet end of the capillary column 30 was transferred from the 100 mM MES/HIS buffer to the buffer reservoir 36 containing H$_2$O. A short plug of H$_2$O was injected into the column 30 by applying $+5$ kV with respect to the outlet end 41 of the column 30 for 30 sec or by gravity injection at 5" for 10 sec. The negative sample ions are injected electrically into the column 30 by transferring the inlet end 31 of the column 30 from the H$_2$O reservoir to the fourth reservoir 33 containing the sample dissolved in the water. A potential of $-5$ kV with respect to the outlet end of the column 30 was then applied for 20 sec. causing a small plug of negative ions to electromigrate into the column. Next, the positive sample ions were injected electrically into the column 30, with the inlet end 31 of column 30 still in the sample reservoir, switching the polarity of the power supply 44 to +5 kV with respect to the outlet end 41 of the column 30 for 10 sec. (Although some negative ions inside the column 30 are caused to migrate out of the column 30 from the inlet end 31, a small plug of positive ions electromigrate into the column 30.) The inlet end 31 of column 30 is then transferred back to 100 mM MES/-HIS buffer and the separation is started by applying 30 kV positive at the inlet end 31 with respect to the outlet end 41 of the column 30.

Figure 5:
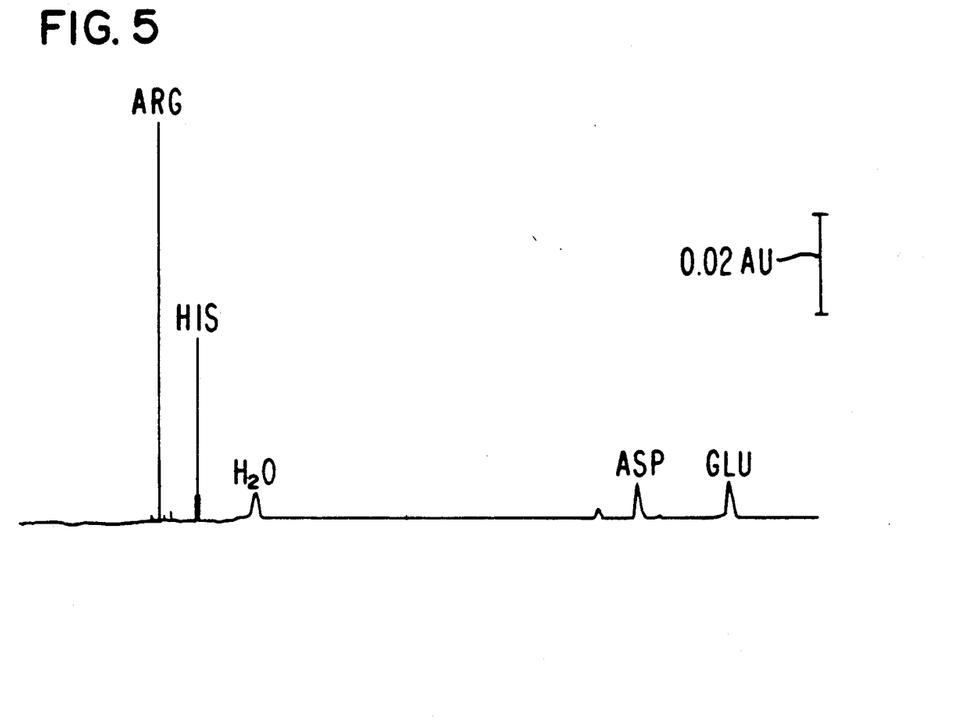
FIG. 5 is a capillary electropherogram of FAPSI with both positive and negative ions.

FIG. 5 is a capillary electropherogram of two positive ions and two negative ions using the method of this invention: Positive-PTH-Arginine (peak 1), PTH-Histidine (peak 2), and Negative-PTH-Aspartic Acid (peak 3), PTH-Glutamic acid (peak 4).

Figure 6:
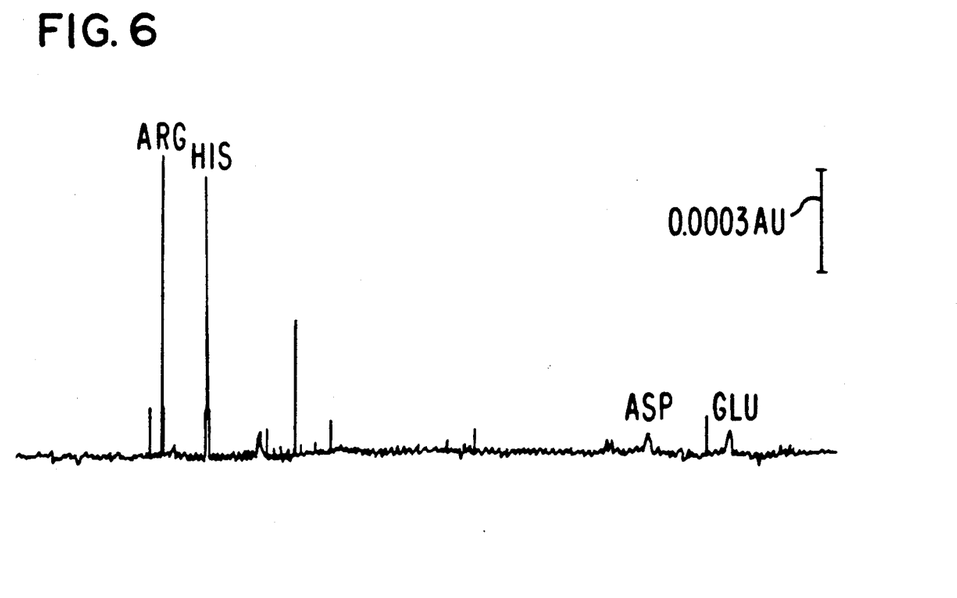
FIG. 6 is a capillary electropherogram of injection, i.e., without field amplification and polarity switching.

For comparison, a electropherogram of the same sample ions using conventional electroinjection, where the sample is prepared in the electrolyte that has the same concentration as the electrolyte inside the capillary column 30 and no polarity switching during injection, is shown in FIG. 6. The detector sensitivity in FIG. 6 is set at sixth four times the sensitivity setting in FIG. 5. Although one can also obtain signals from both positive and the negative ions in conventional electroinjection, the number of ions injected is much smaller than in FAPSI, especially for negative ions.

Figure 7:
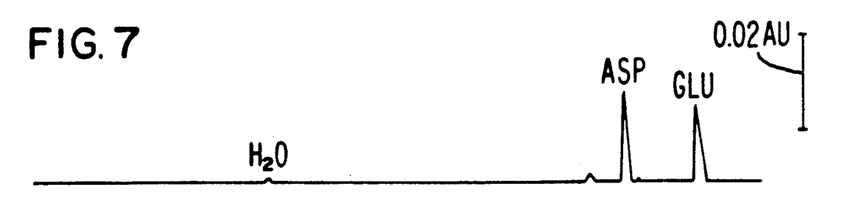
FIG. 7 is a electropherogram with negative ion injection.
Figure 8:
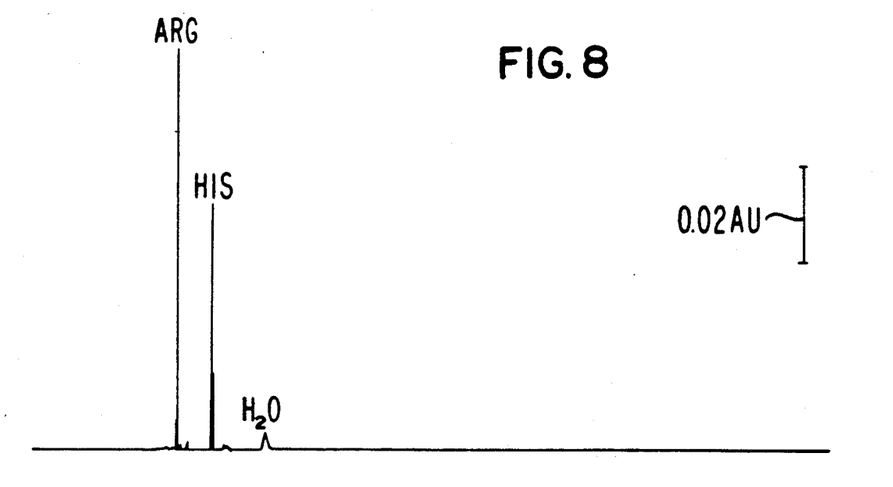
FIG. 8 is a electropherogram with positive ion injection.

FIG. 7 and FIG. 8 are two electropherograms of the same sample solution prepared in $H_2O$ obtained using the charge discrimination injection described earlier. They show a clear charge discrimination against either positive or negative ions. We observe only the negative ions signals in FIG. 7 and only the positive ion signals in FIG. 8.

Figure 9:
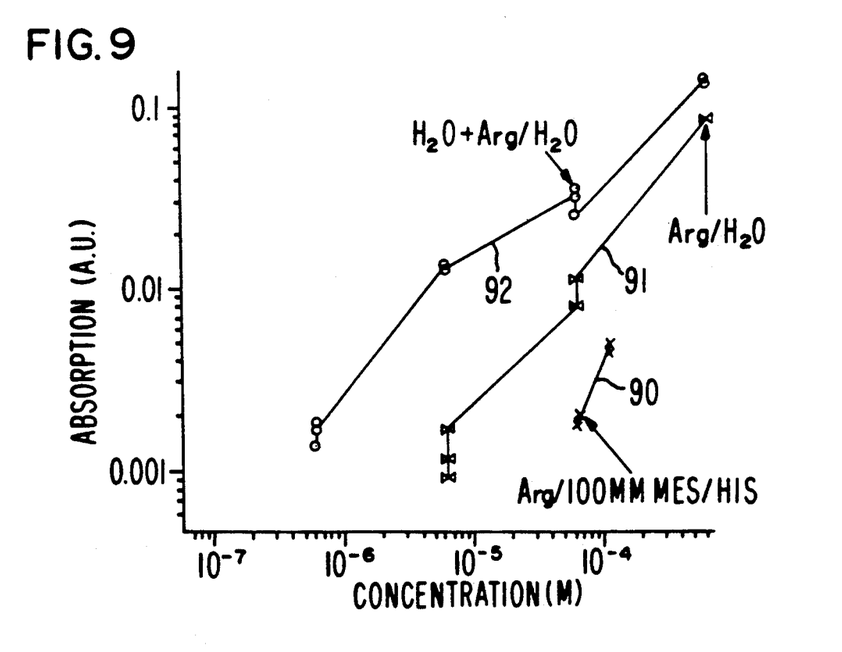
FIG. 9 is a chart showing the enhancement in the CZE signal in FASI.

FIG. 9 shows the enhancement in the signals of PTH-Arginine ions using FASI with a water plug in front of the sample compared with using conventional electroinjection and FASI without water plug. An order of magnitude of improvement in detection limit is obtained between FASI without water plug and conventional electroinjection. Another order of magnitude of improvement in detection limit is obtained between FASI with and without water plug. The trace 90 is conventional electroinjection of PTH-Arginine without a water plug. Trace 91 is for FASI without a water plug. Trace 92 is for FASI with a water plug in front of the sample according to our invention. These results show an improvement in the detection limit for PTH-Arginine from $10^{-5}M$ to $10^{-7}M$.

We claim:

1. A method of introducing a sample into a capillary column in capillary zone electrophoresis comprising the steps of:
   diluting said sample in a first buffer;
   substantially filling a capillary column with a second buffer of higher conductivity than the first buffer, said capillary column having an inlet and outlet end;
   loading a plug of a third buffer of conductivity lower than the second buffer through said inlet end of said capillary column into said capillary column next to and in contact with said second buffer;
   injecting said sample dissolved in said first buffer into said capillary column.

2. The method of claim 1 wherein said third buffer is pure water.

3. The method of claim 1 wherein said third buffer is of comparable or lower conductivity than said first buffer.

4. The method of claim 3 wherein said first buffer is of higher conductivity than said pure water.

5. The method of claim 1 wherein the step of substantially filling said capillary column with said second buffer comprises:
   placing said inlet end of said capillary column into a first reservoir containing said second buffer;
   placing said outlet end of said column into a second reservoir; and
   substantially filling said capillary column with said second buffer by hydrostatic pressure.

6. The method of claim 1 wherein the step of loading a plug of a third buffer comprises:
   transferring the said inlet end of said capillary column from said first reservoir to a third reservoir containing said third buffer; and
   introducing said plug of said third buffer into said capillary column.

7. The method of claim 6 wherein said capillary column is loaded with said plug of said third buffer by applying a voltage across said capillary column for a period which is relatively short in comparison to the analysis time.

8. The method of claim 7 wherein the voltage applied across said capillary column is on the order of 5 kilovolts for a period on the order of thirty seconds.

9. The method of claim 1 wherein the step of injecting said sample includes:
   transferring said inlet end of said capillary column from a third reservoir containing said third buffer to a fourth reservoir, containing said sample dissolved in said first buffer;
   introducing said sample dissolved in said first buffer of said fourth reservoir into said capillary column by applying an electric field across said capillary column.

10. The process for introducing positive ions of the sample into a capillary column comprising the steps of:
    diluting the sample in a first buffer;
    substantially filling a capillary column with a second buffer of higher conductivity than the first buffer, said capillary column having an inlet and outlet end;
    loading a plug of a third buffer of conductivity lower than the second buffer through said inlet end of said capillary column into said capillary column next to and in contact with said second buffer;
    injecting said positive ions of the sample into said capillary column.

11. The process of claim 10 wherein said third buffer is pure water.

12. The method of claim 10 wherein said third buffer is of comparable or lower conductivity than said first buffer.

13. The method of claim 12 wherein said first buffer is of higher conductivity than said pure water.

14. The process of claim 10 wherein the steps of substantially filling said capillary column with said second buffer comprise:
    placing said inlet end of said capillary column into a first reservoir containing said second buffer;
    placing said outlet end of said column into a second reservoir
    substantially filling said capillary column with said second buffer by hydrostatic pressure.

15. The process of claim 10 wherein the step of loading a plug of a third buffer comprises:
   switching the said inlet end of said capillary column from said first reservoir to a third reservoir containing said third buffer;
   introducing said plug of said third buffer into said capillary column.

16. The process of claim 15 wherein said capillary column is filled with said plug of said third buffer by applying a voltage across said capillary column for a period which is relatively short in comparison to the analysis time.

17. The process of claim 16 wherein the voltage applied across said capillary column is on the order of 5 kilovolts for a period on the order of thirty seconds.

18. The process of claim 10 wherein the step of injecting said positive ions of the sample includes:
   transferring said inlet end of said capillary column from a third reservoir containing said third buffer to a fourth reservoir, containing said sample dissolved in said first buffer of higher conductivity than the first buffer;
   introducing said positive ions of the sample dissolved in said first buffer of said fourth reservoir into said capillary column by applying a voltage across said capillary column.

19. The process of claim 18 wherein said capillary column is filled with said positive ions of the sample dissolved in said first buffer by applying a positive voltage at said inlet end of said capillary column across said capillary column for a period which is relatively short in comparison to the analysis time.

20. The process of claim 19 wherein the voltage applied across said capillary column is on the order of 5 kilovolts for a period on the order of ten seconds.

21. The process for introducing a negative ion of the sample into a capillary column comprising the steps of:
   diluting said sample in a first buffer;
   substantially loading into a capillary column a second buffer of higher conductivity than the first buffer, said capillary column having an inlet and outlet end;
   loading a plug of a third buffer through said inlet end of said capillary column into said capillary column next to and in contact with said second buffer;
   injecting said negative ions of the sample into said capillary column.

22. The process of claim 21 wherein said third buffer is pure water.

23. The method of claim 21 wherein said third buffer is of comparable or lower conductivity than said first buffer.

24. The method of claim 23 wherein said first buffer is of higher conductivity than said pure water.

25. The process of claim 21 wherein the step of substantially loading into capillary column said second buffer comprises:
   placing said inlet end of said capillary column into a first reservoir containing said second buffer;
   placing said outlet end of said column into a second reservoir; and
   substantially filling said capillary column with said second buffer by hydrostatic pressure.

26. The process of claim 21 wherein the step of loading a plug of a third buffer comprises:
   transferring the said inlet end of said capillary column from said first reservoir to a third reservoir containing said third buffer; and
   introducing said plug of said third buffer into said capillary column.

27. The process of claim 26 wherein said capillary column is filled with said short plug of said third buffer by applying a voltage across said capillary column for a period which is relatively short in comparison to the analysis time.

28. The process of claim 27 wherein the voltage applied across said capillary column is on the order of 5 kilovolts for a period on the order of thirty seconds.

29. The process of claim 21 wherein the step of injecting said negative ions of the sample includes:
   transferring said inlet end of said capillary column from a third reservoir containing said third buffer to a fourth reservoir containing said sample dissolved in said first buffer;
   introducing said negative ions of the sample dissolved in said first buffer of said fourth reservoir into said capillary column by applying a voltage across said capillary column.

30. The process of claim 21 wherein said capillary column is filled with said negative ions of the sample dissolved in said first buffer by applying a negative voltage at said inlet end of said capillary column across said capillary column for a period which is relatively short in comparison to the analysis time.

31. The process of claim 30 wherein the voltage applied across said capillary column is on the order of 5 kilovolts for a period of ten seconds.

32. The process for introducing both positive and negative ions of a sample into a capillary column comprising the steps of:
   diluting said sample in a first buffer;
   substantially filling a capillary column with a second buffer of higher conductivity than the first buffer, said capillary column having an inlet and outlet end;
   loading a plug of a third buffer of conductivity lower than the second buffer through said inlet end of said capillary column into said capillary column next to and in contact with said second buffer;
   injecting said sample having both positive and negative ions into said capillary column by applying and switching the polarity of the electric field being applied across said capillary column, said positive and negative ions of the sample becoming associated with second buffer through said plug of said third buffer.

33. The process of claim 32 wherein said third buffer is pure water.

34. The method of claim 32 wherein said third buffer is of comparable or lower conductivity than said first buffer.

35. The method of claim 34 wherein said first buffer is of higher conductivity than said pure water.

36. The process of claim 32 wherein the step of substantially filling said capillary column with said second buffer comprises:
   placing said inlet end of said capillary column into a first reservoir containing said second buffer;
   placing said outlet end of said column into a second reservoir; and
   substantially filling said capillary column with said second buffer by hydrostatic pressure.

37. The process of claim 32 wherein the step of loading a plug of a third buffer comprises:

switching the said inlet end of said capillary column from said first reservoir to a third reservoir containing said third buffer; and introducing said plug said third buffer into said capillary column.

38. The process of claim 37 wherein said capillary column is filled with said plug of said third buffer by applying a voltage across said capillary column for a period which is relatively short in comparison to the analysis time.

39. The process of claim 38 wherein the voltage applied across said capillary column is on the order of 5 kilovolts for a period on the order of thirty seconds.

40. The process of claim 32 wherein the step of injecting said positive and negative ions includes:

applying a negative voltage at the said inlet end of said capillary column on the order of 5 kilovolts across said capillary column for a period on the order of twenty seconds in order to inject negative ions first.

41. The process of claim 40 wherein said step of injecting said positive and negative ions includes:

applying a positive voltage at said inlet end of said capillary column on the order of 5 kilovolts across said capillary column for a period on the order of ten seconds in order to inject positive ions first.

42. The process of claim 40 wherein the step of injecting said positive and negative ions of the sample includes:

switching the polarity of the said voltage across said capillary column.

43. The process of claim 41 wherein the step of injecting said positive and negative ions of the sample includes:

switching the polarity of said voltage across said capillary column.

* * * * *